(12) United States Patent
Matthews et al.

(10) Patent No.: US 10,286,165 B2
(45) Date of Patent: May 14, 2019

(54) STARTING PRESSURE FOR RESPIRATORY THERAPY DEVICES

(71) Applicant: KONINKLIJKE PHILIPS N.V., Eindhoven (NL)

(72) Inventors: Gregory Delano Matthews, Pittsburgh, PA (US); Benjamin Irwin Shelly, Pittsburgh, PA (US); Heather Dawn Ressler, Blairsville, PA (US); Michael Thomas Kane, Harrison City, PA (US); Mark Dominic D'Angelo, Harrison City, PA (US); Zachary Dean Paul, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 588 days.

(21) Appl. No.: 14/387,108

(22) PCT Filed: Mar. 26, 2013

(86) PCT No.: PCT/IB2013/052382
§ 371 (c)(1),
(2) Date: Sep. 22, 2014

(87) PCT Pub. No.: WO2013/144827
PCT Pub. Date: Oct. 3, 2013

(65) Prior Publication Data
US 2015/0040903 A1 Feb. 12, 2015

Related U.S. Application Data

(60) Provisional application No. 61/617,881, filed on Mar. 30, 2012.

(51) Int. Cl.
*A61M 16/00* (2006.01)
*A61M 16/16* (2006.01)
(Continued)

(52) U.S. Cl.
CPC .... *A61M 16/0003* (2014.02); *A61M 16/0051* (2013.01); *A61M 16/0066* (2013.01);
(Continued)

(58) Field of Classification Search
CPC .......... A61M 16/0003; A61M 16/0066; A61M 16/06; A61M 16/0875; A61M 16/0069;
(Continued)

(56) References Cited

U.S. PATENT DOCUMENTS 6,401,713 B1   6/2002  Hill et al.
6,988,498 B2 * 1/2006  Berthon-Jones ...... A61M 16/00
                                                  128/204.18
(Continued)

FOREIGN PATENT DOCUMENTS

WO   2012024733 A2   3/2012

*Primary Examiner* — Gregory A Anderson
*Assistant Examiner* — Margaret M Luarca

(57) ABSTRACT

Systems and methods for providing respiratory therapy to a subject respond and/or adapt to the detection of an occurrence of a respiratory event. For example, the pressure level of a pressurized flow of breathable gas may be increased responsive to the occurrence of one or more apneas. Based on usage information spanning more than one therapy session, such as the tracked pressure levels, a starting pressure level for a pressurized flow of breathable gas for a subsequent therapy session is determined. The starting level at the beginning of the subsequent therapy session(s) may be the 90% pressure level as determined during the preceding period during which usage information has been gathered.

15 Claims, 4 Drawing Sheets

(51) Int. Cl.
  *A61M 16/06* (2006.01)
  *A61M 16/08* (2006.01)

(52) U.S. Cl.
  CPC ...... *A61M 16/0069* (2014.02); *A61M 16/024* (2017.08); *A61M 16/06* (2013.01); *A61M 16/0875* (2013.01); *A61M 16/161* (2014.02); *A61M 2016/0021* (2013.01); *A61M 2016/0027* (2013.01); *A61M 2016/0036* (2013.01); *A61M 2016/0039* (2013.01); *A61M 2205/332* (2013.01); *A61M 2205/3303* (2013.01); *A61M 2205/3365* (2013.01); *A61M 2205/52* (2013.01); *A61M 2230/005* (2013.01); *A61M 2230/43* (2013.01); *A61M 2230/432* (2013.01)

(58) Field of Classification Search
  CPC ........ A61M 2230/005; A61M 2205/52; A61M 2016/0027; A61M 2016/0039
  See application file for complete search history.

(56) References Cited

U.S. PATENT DOCUMENTS

| | | |
|---|---|---|
| 7,469,698 B1 | 12/2008 | Childers |
| 2002/0056452 A1 | 5/2002 | Brewer et al. |
| 2004/0187870 A1* | 9/2004 | Matthews ......... A61M 16/0051 128/204.22 |
| 2007/0142741 A1 | 6/2007 | Bassin et al. |
| 2007/0221224 A1 | 9/2007 | Pittman et al. |
| 2008/0053440 A1* | 3/2008 | Farrugia ............... A61M 16/00 128/204.23 |
| 2009/0038616 A1 | 2/2009 | Mulcahy et al. |
| 2009/0173347 A1 | 7/2009 | Berthon-Jones |
| 2009/0205662 A1 | 8/2009 | Kwok et al. |
| 2010/0049008 A1 | 2/2010 | Doherty et al. |
| 2011/0155134 A1 | 6/2011 | Farrugia |

\* cited by examiner

STARTING PRESSURE FOR RESPIRATORY THERAPY DEVICES

BACKGROUND

1. Field

The present disclosure pertains to systems and methods for providing respiratory therapy of a subject. In particular, the present disclosure pertains to determining a smart starting level for a pressurized flow of breathable gas at the beginning of a therapy session, based on prior usage.

2. Description of the Related Art

It is well known that some types of respiratory therapy involve the delivery of a flow of breathable gas to the airway of a subject. It is known that a therapy session may commonly span eight or more hours, and may be intended to coincide and/or overlap, at least in part, with a subject's daily and/or nightly sleeping period. It is known that a subject's comfort during a therapy session is an important factor in therapy adoption rates and/or therapy success rates. It is known that a flow of breathable gas may be pressurized at varying levels of pressure, even during a single therapy session. It is known that respiratory events, in particular common events during sleep, may be prevented by increasing levels of pressure for the pressurized flow. It is known that increasing pressure levels have various downsides, including but not limited to reduced comfort. It is known that algorithms may operate to control the pressure level used in respiratory therapy during a therapy session. It is known that such algorithms may autonomously and/or automatically change the pressure level based on various conditions, settings, and/or occurrences of respiratory events. It is known that such algorithms may operate within a range of permitted pressure levels, including a minimum level and a maximum level that form the boundaries of such a range. It is known that many such algorithms reset the pressure level at the beginning of a therapy session to the minimum level.

SUMMARY

Accordingly, it is an object of one or more embodiments of the present invention to provide a system to provide respiratory therapy of a subject having an airway. The system includes a pressure generator configured to generate a pressurized flow for delivery to the airway of the subject during respiratory therapy, wherein the pressurized flow includes breathable gas; one or more sensors configured to generate one or more output signals conveying information related to one or more gas parameters of the pressurized flow; and one or more processors configured to execute processing modules, the processing modules comprising: a control module configured to control the pressure generator to provide the pressurized flow during a therapy session; a therapy module configured to adjust levels of one or more gas parameters of the pressurized flow; a usage module configured to gather usage information based on the provided pressurized flow; and a starting level module configured to determine a starting level of one or more gas parameters of the pressurized flow, wherein the determination is based on the gathered usage information, wherein the usage information corresponds to therapeutic usage of the system spanning at least a threshold amount of usage, wherein the threshold amount of usage is more than one therapy session. The therapy module may be further configured to apply the starting level at a beginning of a therapy session.

It is yet another aspect of one or more embodiments of the present invention to provide a method for providing respiratory therapy of a subject having an airway. The method includes generating a pressurized flow for delivery to the airway of the subject during respiratory therapy, wherein the pressurized flow includes breathable gas; generating one or more output signals conveying information related to one or more gas parameters of the pressurized flow; providing the pressurized flow to the subject during a therapy session; adjusting levels of one or more gas parameters of the pressurized flow; gathering usage information based on the provided pressurized flow; determining a starting level of one or more gas parameters of the pressurized flow, wherein the determination is based on the gathered usage information, wherein the usage information corresponds to respiratory therapy spanning at least a threshold amount of usage, wherein the threshold amount of usage is more than one therapy session; and applying the starting level at a beginning of a therapy session.

It is yet another aspect of one or more embodiments to provide a system configured to provide respiratory therapy of a subject having an airway. The system includes means for generating a pressurized flow for delivery to the airway of the subject during respiratory therapy, wherein the pressurized flow includes breathable gas; means for generating one or more output signals conveying information related to one or more gas parameters of the pressurized flow; means for providing the pressurized flow to the subject during a therapy session; means for adjusting levels of one or more gas parameters of the pressurized flow; means for gathering usage information based on the provided pressurized flow; means for determining a starting level of one or more gas parameters of the pressurized flow, wherein the determination is based on the gathered usage information, wherein the usage information corresponds to respiratory therapy spanning at least a threshold amount of usage, wherein the threshold amount of usage is more than one therapy session; and means for applying the starting level at a beginning of a therapy session.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
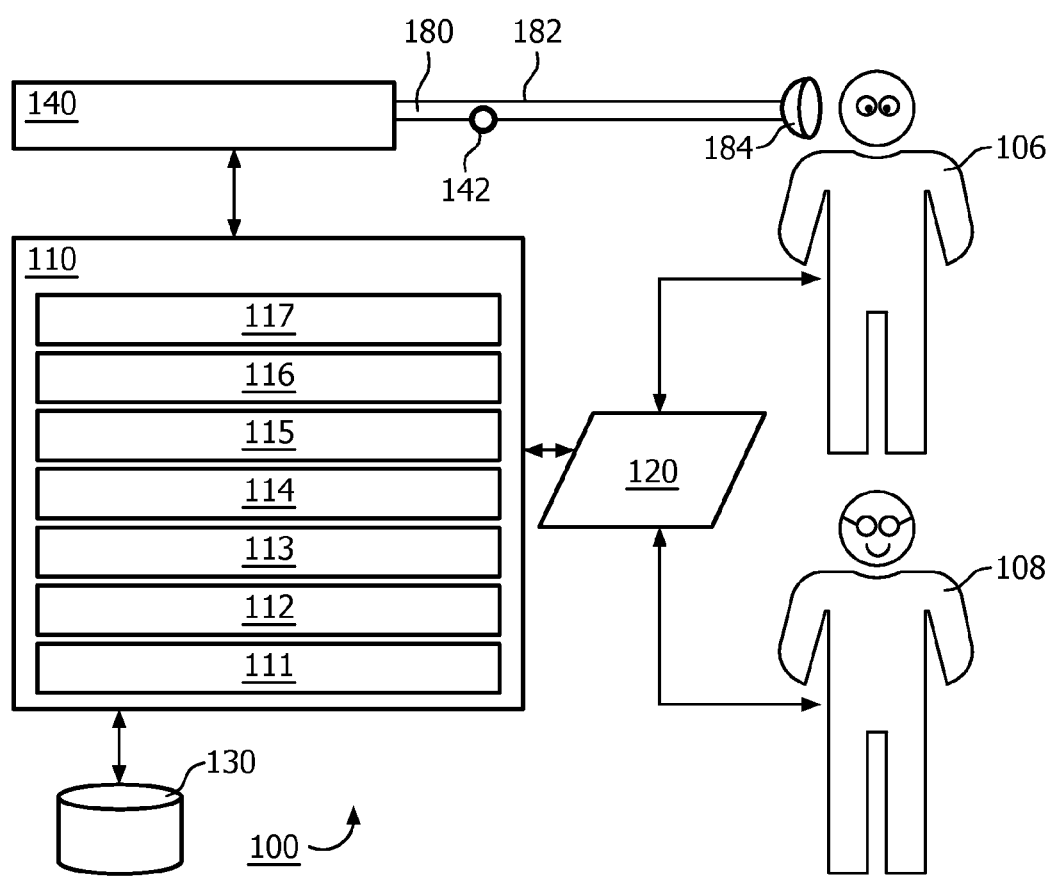
FIG. 1 schematically illustrates a system configured to provide respiratory therapy of a subject, according to certain embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

As used herein, the word "unitary" means a component is created as a single piece or unit. That is, a component that includes pieces that are created separately and then coupled as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 100 configured to provide respiratory therapy to the airway of a subject 106. System 100 may be implemented as, integrated with, and/or operating in conjunction with a respiratory therapy device. System 100 uses gathered usage information, pertaining to subject 106 using system 100, to determine smart starting levels to apply to subsequent sessions of respiratory therapy.

A therapy "session" of using system 100 may be defined as a period of substantially uninterrupted therapeutic usage of system 100, not to exceed some upper threshold of (consecutive) hours. The upper threshold may be, for example, about 10 hours, about 12 hours, about 16 hours, about 24 hours and/or other time periods. If the respiratory therapy is used to treat sleeping disorders the related session length may correspond to the sleeping pattern of a subject. A typical session length may thus be about eight hours. Alternatively, and/or simultaneously, a therapy session may be defined as a period of substantially uninterrupted therapeutic usage of system 100, not to span less than some lower threshold of (consecutive) units of time, and/or at least a minimum period of time apart from a previous session. For example, a minute of usage may be too short to be regarded as a session. For example, two 4-hour periods of usage separated by a 15-minute gap may be regarded as one session rather than two sessions. Individual therapy sessions may have a beginning and an end.

In some embodiments, one or more operative levels (e.g. pressure, volume, etc.) are adjusted on a relatively ongoing manner (e.g., each breath, every few breaths, every few seconds, etc.) during an individual therapy session to titrate the therapy. Alternatively, and/or simultaneously, adjustments may be made more intermittently and/or only between therapy sessions rather than during therapy sessions.

System 100 includes one or more of a pressure generator 140, a delivery circuit 180, one or more sensors 142, an electronic storage 130, a user interface 120, a processor 110, a control module 111, a respiratory event module 112, a therapy module 113, a usage module 114, a starting level module 115, a parameter determination module 116, a timing module 117, and/or other components.

Pressure generator 140 of system 100 in FIG. 1 may be integrated, combined, or connected with a ventilator and/or (positive) airway pressure device (PAP/CPAP/BiPAP®/etc.) and configured to provide a pressurized flow of breathable gas for delivery to the airway of subject 106, e.g. via delivery circuit 180. Delivery circuit 180 may sometimes be referred to as subject interface 180. Subject 106 may or may not initiate one or more phases of respiration. Respiratory therapy may be implemented as pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas. Pressure generator 140 is configured to adjust one or more of pressure levels, flow, humidity, velocity, acceleration, and/or other parameters of the pressurized flow of breathable gas, e.g. in substantial synchronization with the breathing cycle of the subject.

A pressurized flow of breathable gas is delivered from pressure generator 140 to the airway of subject 106 via a delivery circuit 180. Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 of system 100 in FIG. 1 is configured to deliver the pressurized flow of breathable gas to the airway of subject 106. As such, subject interface appliance 184 may include any appliance suitable for this function. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

Electronic storage 130 of system 100 in FIG. 1 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.).

Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store one or more gas and/or respiratory parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed to user 108 is a report detailing occurrences of respiratory events throughout a period during which the subject is receiving therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize system 100. Other exemplary input devices and techniques adapted for use with system 100 as user interface 120 include, but are not limited to, an RS-232 port, RF link, an IR link, modem (telephone, cable, Ethernet, internet or other). In short, any technique for communicating information with system 100 is contemplated as user interface 120.

One or more sensors 142 of system 100 in FIG. 1 are configured to generate output signals conveying measurements related to parameters of respiratory airflow and/or airway mechanics. These parameters may include one or more of flow, (airway) pressure, humidity, velocity, acceleration, and/or other parameters. Sensor 142 may be in fluid communication with conduit 182 and/or subject interface appliance 184. Sensor 142 may generate output signals related to physiological parameters pertaining to subject 106.

The illustration of sensor 142 including a single member in FIG. 1 is not intended to be limiting. The illustration of sensor 142 at or near subject interface appliance 184 is not intended to be limiting. In one embodiment sensor 142 includes a plurality of sensors operating as described above by generating output signals conveying information related to parameters associated with the state and/or condition of an airway of subject 106, the breathing of subject 106, the gas breathed by subject 106, the composition of the gas breathed by subject 106, the delivery of the gas to the airway of subject 106, and/or a respiratory effort by the subject. For example, a parameter may be related to a mechanical unit of measurement of a component of pressure generator 140 (or of a device that pressure generator 140 is integrated, combined, or connected with) such as valve drive current, rotor speed, motor speed, blower speed, fan speed, or a related measurement that may serve as a proxy for any of the previously listed parameters through a previously known and/or calibrated mathematical relationship. Resulting signals or information from one or more sensors 142 may be transmitted to processor 110, user interface 120, electronic storage 130, and/or other components of system 100. This transmission may be wired and/or wireless.

Processor 110 of system 100 in FIG. 1 is configured to provide information processing capabilities in system 100. As such, processor 110 includes one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of control module 111, respiratory event module 112, therapy module 113, usage module 114, starting level module 115, parameter determination module 116, timing module 117, and/or other modules. Processor 110 may be configured to execute modules 111-117 by software; hardware; firmware; some combination of software, hardware, and/or firmware; and/or other mechanisms for configuring processing capabilities on processor 110.

It should be appreciated that although modules 111-117 are illustrated in FIG. 1 as being co-located within a single processing unit, in embodiments in which processor 110 includes multiple processing units, one or more of modules 111-117 may be located remotely from the other modules. The description of the functionality provided by the different modules 111-117 described herein is for illustrative purposes, and is not intended to be limiting, as any of modules 111-117 may provide more or less functionality than is described. For example, one or more of modules 111-117 may be eliminated, and some or all of its functionality may be incorporated, shared, integrated into, and/or otherwise provided by other ones of modules 111-117. Note that processor 110 may be configured to execute one or more additional modules that may perform some or all of the functionality attributed below to one of modules 111-117.

Parameter determination module 116 of system 100 in FIG. 1 is configured to determine one or more gas parameters, breathing parameters, and/or other parameters from output signals generated by sensor(s) 142. The one or more gas parameter may include and/or be related to one or more of (peak) flow, flow rate, (tidal) volume, pressure, temperature, humidity, velocity, acceleration, gas composition (e.g. concentration(s) of one or more constituents such as, e.g., $CO_2$), thermal energy dissipated, (intentional) gas leak, and/or other measurements related to the (pressurized) flow of breathable gas. One or more breathing parameters may be derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), and/or other breathing parameters.

Timing module 117 is configured to determine whether a current respiratory phase of subject 106 is an inhalation phase or an exhalation phase. In some embodiments, timing module 117 may be configured to determine respiratory timing parameters and/or other timing parameters related to the operation of system 100, such as transitions in breathing between inhalations and exhalations. Respiratory timing parameters may include transitional moments that separate inhalation phases from exhalation phases and/or vice versa, breathing period, respiratory rate, inhalation time or period, exhalation time or period, start and/or end of inhalation phases, start and/or end of exhalation phases, and/or other respiratory timing parameters. Timing parameters related to the operation of system 100 may include therapy session length, session start time, session stop time, average and/or cumulative daily and/or nightly usage, amount of usage since the most recent pressure adjustment, and/or other timing parameters related to the operation of system 100.

Control module 111 is configured to control operation of system 100 during a therapy session. Control module 111 may be configured to control the pressure generator to adjust one or more levels of gas parameters of the pressurized flow of breathable gas in accordance with one or more of a (respiratory) therapy regimen, level adjustments by therapy module 113, starting levels determined by starting module 115, one or more algorithms that control adjustments and/or changes in the pressurized flow of breathable gas, and/or other factors. Control module 111 may be configured to control pressure generator 140 to provide the pressurized flow of breathable gas. Control module 111 may be configured to control pressure generator 140 such that one or more gas parameters of the pressurized flow of breathable gas are varied over time in accordance with a respiratory therapy regimen. Control module 111 may be configured to control pressure generator 140 to provide the pressurized flow of breathable gas at inhalation pressure levels during inhalation phases, and/or at exhalation pressure levels during exhalation phases. Parameters determined by parameter determination module 116, timing module 117, and/or received through sensors 142 may be used by control module 111, e.g. in a feedback manner, to adjust one or more therapy modes/settings/operations of system 100. Alternatively, and/or simultaneously, signals and/or information received through user interface 120 may be used by control module 111, e.g. in a feedback manner, to adjust one or more therapy modes/settings/operations of system 100. Control module 111 may be configured to time its operations relative to the transitional moments in the breathing cycle of a subject, over multiple breath cycles, and/or in any other relation to any detected occurrences or determinations by timing module 117.

Respiratory event module 112 is configured to detect occurrences of respiratory events, e.g. based on output signals generated by sensor 142. Respiratory event module 112 may be configured to detect occurrences of respiratory events based on parameters determined by parameter determination module 111. For example, respiratory event module 112 may detect occurrences of Cheyne-Stokes respiration, central apneas, obstructive apneas, hypopneas, snoring, hyperventilation, arousals, lack (or significantly reduced level) of respiratory effort, respiratory effort related arousals (RERAs), and/or other respiratory events. Such an occurrence may be used, automatically, autonomously, and/or manually, to alter the operating parameters of system 100 and/or its constituent components. In some embodiments, respiratory event module 112 may be configured to detect conditions that are indicative of a likely and/or imminent respiratory event. For example, one or more breathing parameters may indicate that subject 106 is likely to suffer an apnea very soon, though a particular adjustment in one or more levels of one or more gas parameters of the pressurized flow of breathable gas may prevent that apnea.

Therapy module 113 is configured to adjust levels of one or more gas parameters of the pressurized flow of breathable gas such that an adjustment is based on a detected occurrence of a respiratory event. Threshold module 113 may be further configured to apply a starting level, e.g. such as determined by starting level module 115, at a beginning of a therapy session. In some embodiments, therapy module 113 may run and/or control a titrating algorithm to adjust levels of gas parameters throughout a therapy session. Titration and/or other adjustments may be performed in accordance with a therapy regimen and/or operating guidelines. For example, inspiratory pressure support may be adjusted within a range of pressures, having a minimum level and a maximum level of inspiratory pressure.

Figure 3A:
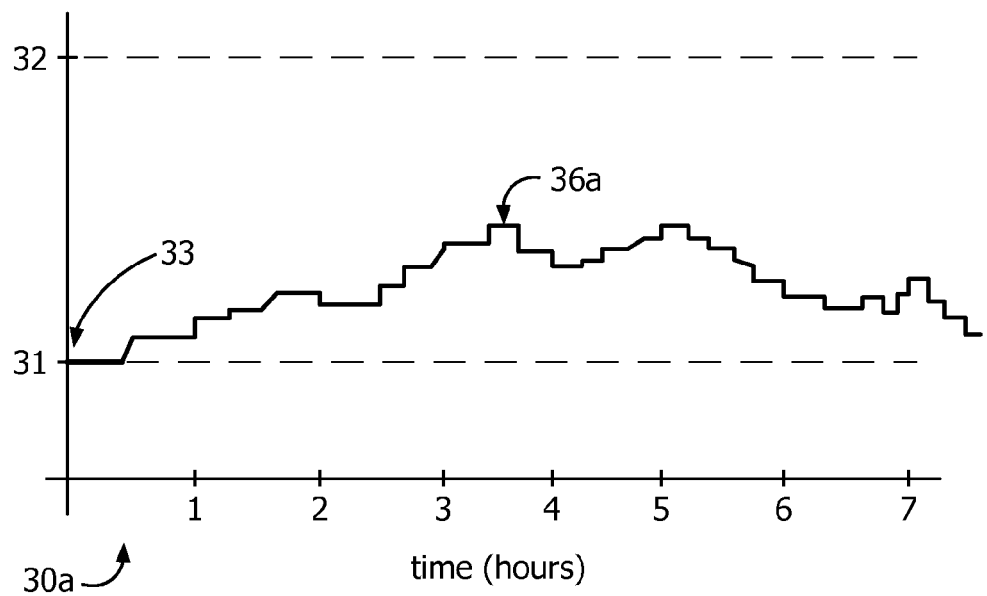
FIG. 3A-3B illustrate exemplary diagrams of pressure levels provided during therapy sessions of respiratory therapy, according to certain embodiments.

By way of illustration, FIG. 3A illustrates a diagram 30a of a pressure level 36a as it varies over time for a particular therapy session spanning approximately over seven hours. In this example, pressure level 36a may be bound within a range defined by a maximum pressure level 32 and a minimum pressure level 31. A pressure level 33 at the start of the particular therapy session in diagram 30a is equal to the minimum pressure level 31. Pressure level 36a titrates up during, approximately, the first two hours depicted in FIG. 3A.

Returning to FIG. 1, usage module 114 is configured to gather usage information based on the provided pressurized flow of breathable gas. Gathered usage information may be used for particular purposes by other modules, such as, e.g., starting level module 115. Usage module 114 may be configured to retain only a certain amount of historic usage information.

The gathered usage information used for a particular purpose may correspond to therapeutic usage of system 100 spanning at least a threshold amount of usage. The threshold amount of usage may be a predetermined amount of therapeutic usage. The predetermined amount of usage may be an hour, two hours, four hours, eight hours, ten hours, fifteen hours, 20 hours, 25 hours, 30 hours, 35 hours, 40 hours, 50 hours, about one therapy session, more than about one therapy session, more than about two therapy sessions, more than about four therapy sessions, about a week of therapy sessions, and/or another amount of therapeutic usage, or any combination thereof. For example, the predetermined amount of usage may be at least 25 hours, rounded up to the next completed session. The predetermined amount of therapeutic usage used as the threshold amount may be constant across multiple sessions, weeks of usage, and/or months of usage. Alternatively, the predetermined amount of therapeutic usage used as the threshold amount may vary according to various factors, including, but not limited to, patient feedback, input from a medical professional, amount of system usage, and/or other factors.

The gathered usage information used for a particular purpose may pertain to one or more levels of one or more gas parameters of the provided pressurized flow of breathable gas. For example, the gathered usage information may pertain to the level of (inspiratory) pressure of the pressurized flow of gas, historical pressure level, average pressure level, mean/median pressure level, a $90^{th}$ percentile pressure level, a $95^{th}$ percentile pressure level, a predetermined percentile pressure level, a predetermined range of percentile pressure levels, and/or another statistical metric based on the historic pressure level. Note that this exemplary use of the pressure level is not intended to be limiting in any way. The amount of historic information used to gather usage information may, e.g., correspond to the threshold amount of therapeutic usage, described above. For example, in some embodiments, the $90^{th}$ percentile pressure level may correspond to a sliding window of the most recent 30 hours of usage, the most recent four therapy sessions, and/or other predetermined amount of therapeutic usage or combination thereof. Alternatively, such a window of historic information may have a fixed starting point, such as the beginning of a particular therapy session. Note that using too much historic information, e.g. all usage since the start of respiratory therapy, may decrease the responsiveness of system 100 to changing conditions.

Starting level module 115 is configured to determine one or more starting levels of one or more gas parameters of the pressurized flow of breathable gas. Starting levels may pertain to the starting level of one or more gas parameters of the provided pressurized flow of breathable gas at the beginning of a therapy session, e.g. at the beginning of the therapy session following the determination of a particular starting level. Determinations by starting level module 115 are based on usage information gathered by usage module 114. For example, the particular purpose for which usage information is gathered by usage module 114 may be to determine a starting level by starting level module 115, as described herein. In some embodiments, consecutive adjustments of a starting level may be determined and/or applied at least a threshold amount of therapeutic usage of system 100 apart. For example, this threshold amount may be the same threshold amount as described in relation to usage module 114. In some embodiments, consecutive adjustments of a starting level may be determined and/or applied a different threshold amount of usage apart. Application of a starting level may be performed by therapy module 113.

Figure 4:
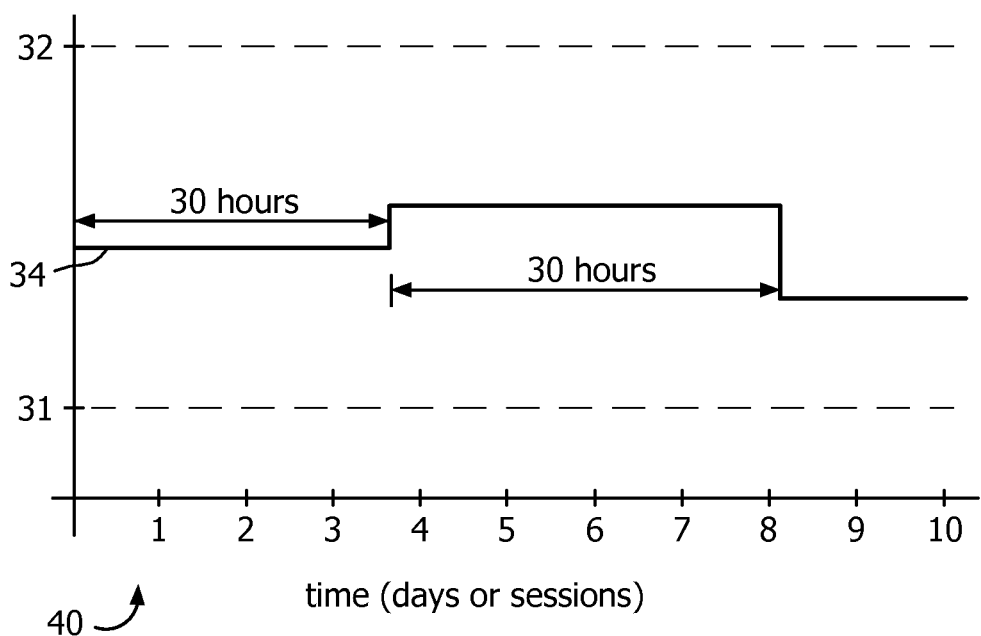
FIG. 4 illustrates an exemplary diagram depicting the changing starting level of a particular gas parameter over time.

By way of illustration, FIG. 4 illustrates a diagram 40 depicting a starting pressure level 34 as it changes over time. In this example, starting pressure level 34 may be bound within a range defined by a maximum pressure level 32 and a minimum pressure level 31. Time in FIG. 4 may reflect days of respiratory therapy or therapy sessions, depending on the implementation. As depicted in this example, adjustments of starting pressure level 34 are determined and/or applied approximately 30 hours of therapeutic usage apart. In this example, 30 hours may be the threshold amount that subsequent adjustments are designed to be apart, as described elsewhere herein in relation to FIG. 1. Note that adjustments may be made during a therapy session.

Returning to starting level module 115 and FIG. 1, in some embodiments, one or more determined starting levels of one or more gas parameters may be factors in an algorithm used to adjust levels of gas parameters throughout a therapy session. For example, a particular determined starting level—which may or may not be the same determined starting level as used at the beginning of a therapy session—may be used in a titrating algorithm that is controlled by therapy module 113. In some embodiments, the algorithm may operate more aggressively depending on the current level of a gas parameter in comparison to a determined starting level for that gas parameter. For example, the algorithm may operate more aggressively responsive to the current pressure level being lower than the particular determined starting pressure level. "Operating" the algorithm may include responding to occurrences of respiratory events detected by respiratory event module 112.

Operating "more aggressively" may include larger adjustments in the level of one or more gas parameters of the pressurized flow of breathable gas, more frequent adjustments therein, more sensitive and/or responsive triggers corresponding to adjustments therein, and/or other ways in which the algorithm may respond to operating conditions more aggressively. For example, operating "more aggressively" may include titrating to a higher pressure level in response to a predetermined number of respiratory events, wherein the predetermined number is relatively lower when the current pressure level is below the particular determined starting pressure level, and/or relatively higher when the current pressure level is above the particular determined starting pressure level. In some embodiments, aggressiveness may be defined using multiple levels such that "operating" the algorithm "more aggressively" may depend on the relation of the current pressure level and the particular determined starting pressure level. For example, the aggressiveness of the operation of the algorithm may increase as the difference between the current pressure level and a particular determined starting pressure level increases. In some embodiments, a determined starting level for a therapy session (and/or a pressure level based thereon) may function as a new minimum pressure level for the range of permitted pressure levels within which an algorithm operates.

Figure 3B:
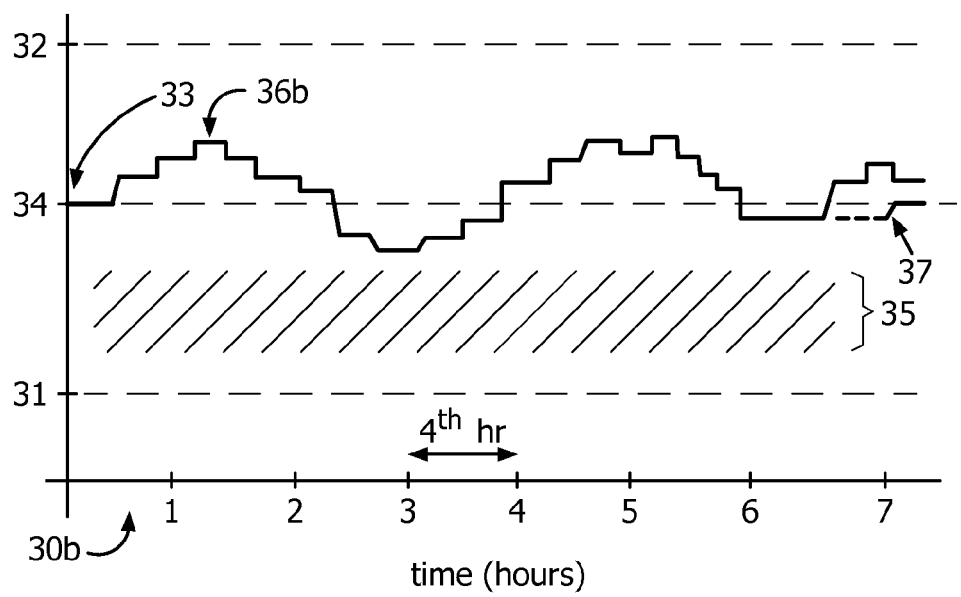

By way of illustration, and in contrast to FIG. 3A, FIG. 3B illustrates a diagram 30b of a pressure level 36b as it varies over time for a particular therapy session spanning approximately over seven hours. In this example, pressure level 36b may be bound within a range defined by a maximum pressure level 32 and a minimum pressure level 31. A pressure level 33 at the start of the particular therapy session in diagram 30b is equal to a starting pressure level 34, which may be determined based on gathered usage information pertaining to the provided pressurized flow in at least one preceding therapy session. For example, starting pressure level 34 may have been determined by a starting level module similar to or substantially the same as starting level module 115 described elsewhere herein in relation to FIG. 1.

Returning to FIG. 3B, pressure level 36b titrates up during, approximately, at least about the first hour depicted in FIG. 3B. The range of pressure levels between minimum pressure level 31 and starting pressure level 34 are indicated as range 35. When pressure level 36b is within range 35, titration may be performed more aggressively than when pressure level 36b is above range 35, as described elsewhere herein. As an example, when pressure level 36b is within range 35, titrating up to a higher pressure level may be performed after fewer detected occurrences of respiratory events than compared to a similar circumstance when pressure level 36b is above range 35. Alternatively, and/or simultaneously, titration example 37 depicted in FIG. 3B illustrates an implementation wherein a titration to a higher pressure level increases pressure level 36b from a level in range 35 directly to starting pressure level 34. This may be in contrast, for example, to the gradual increases in pressure level 36b as depicted in, approximately, the fourth hour of the particular therapy session illustrated in FIG. 3B. As depicted in FIG. 3B, no adjustments of starting pressure level 34 are illustrated. This is not intended to be limiting in any way. Such adjustments are illustrated in FIG. 4.

Figure 2:
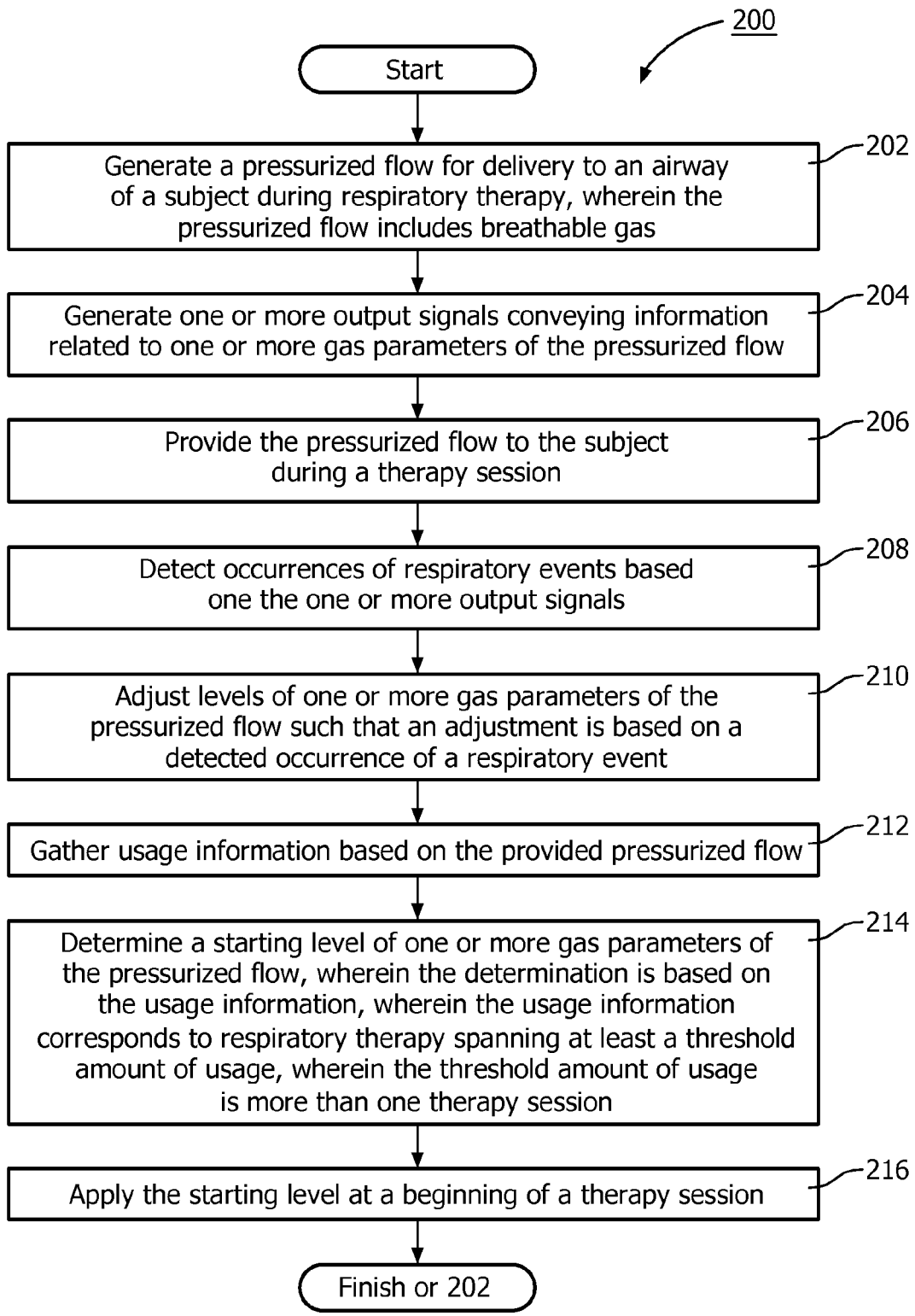
FIG. 2 illustrates a method for providing ventilation to the airway of a subject through a ventilation system, according to certain embodiments.

FIG. 2 illustrates a method for providing respiratory therapy to the airway of a subject. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is generated for delivery to the airway of a subject. In one embodiment, operation 202 is performed by a pressure generator similar to or substantially the same as pressure generator 140 (shown in FIG. 1 and described above).

At an operation 204, one or more output signals are generated that convey information related to one or more gas parameters of the pressurized flow of breathable gas. In one embodiment, operation 204 is performed by a sensor similar to or substantially the same as sensor 142 (shown in FIG. 1 and described above).

At an operation 206, the pressurized flow of breathable gas is provided and/or controlled to be provided to the subject during a therapy session. In one embodiment, operation 206 is performed by a control module similar to or substantially the same as control module 111 (shown in FIG. 1 and described above).

At an operation 208, occurrences of respiratory events are detected based on the one or more output signals. In one embodiment, operation 208 is performed by a respiratory event module similar to or substantially the same as respiratory event module 112 (shown in FIG. 1 and described above).

At an operation 210, levels of one or more gas parameters of the pressurized flow of breathable gas are adjusted based on one or more detected occurrences of one or more respiratory events. In one embodiment, operation 210 is performed by a therapy module similar to or substantially the same as therapy module 113 (shown in FIG. 1 and described above).

At an operation 212, usage information is gathered based on the provided pressurized flow of breathable gas. In one embodiment, operation 212 is performed by a usage module similar to or substantially the same as usage module 114 (shown in FIG. 1 and described above).

At an operation 214, a starting level of one or more gas parameters of the pressurized flow of breathable gas is determined based on the usage information. The usage information corresponds to respiratory therapy spanning at least a threshold amount of usage, wherein the threshold amount of usage is more than one therapy session. In one embodiment, operation 214 is performed by a starting level module similar to or substantially the same as starting level module 115 (shown in FIG. 1 and described above).

At an operation 216, the starting level is applied at a beginning of a therapy session. Method 200 may proceed at operation 202, such that method 200 is performed for subsequent therapy sessions. In one embodiment, operation 216 is performed by a therapy module similar to or substantially the same as therapy module 113 (shown in FIG. 1 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to provide respiratory therapy of a subject having an airway, the system comprising:
   a pressure generator configured to generate a pressurized flow for delivery to the airway of the subject during respiratory therapy, wherein the pressurized flow includes breathable gas;
   one or more sensors configured to generate one or more output signals conveying information related to one or more gas parameters of the pressurized flow; and
   one or more processors configured by machine-readable instructions to:
      control the pressure generator to provide the pressurized flow during a therapy session;
      adjust levels of one or more gas parameters of the pressurized flow, wherein the levels of one or more gas parameters of the pressurized flow include a current pressure level of the pressurized flow, wherein controlling the pressure generator comprises increasing and/or decreasing the current pressure level of the pressurized flow;
      gather usage information based on the provided pressurized flow;
      determine a starting level of one or more gas parameters of the pressurized flow, the starting level configured to be changeable from therapy session to therapy session, wherein the determination is based on gathered usage information, wherein the gathered usage information corresponds to therapeutic usage of the system spanning at least a threshold amount of usage, wherein the threshold amount of usage is more than one therapy session, wherein the gathered usage information includes a pressure level of the pressurized flow, and wherein the starting level of one or more gas parameters of the pressurized flow includes a current starting pressure level, the current starting pressure level configured to be changeable from therapy session to therapy session based on the gathered usage information;

apply the starting level at a beginning of the therapy session such that the current pressure level of the pressurized flow is increased and/or decreased from the current starting pressure level;

detect occurrences of respiratory events based on the one or more output signals; and titrate the current pressure level of the pressurized flow to a higher pressure level based on a predetermined number of respiratory events, wherein the predetermined number of respiratory events when the current pressure level is less than the current starting pressure level is lower than the predetermined number of respiratory events when the current pressure level is greater than the current starting pressure level, wherein:

adjustments of the current pressure level are controlled by the one or more processors, responsive to the current pressure level being below the current starting pressure level, the one or more processors cause adjustment using an increased pressure increment compared to a pressure increment used responsive to the current pressure level being above the current starting pressure level, and the increased pressure increment increases in relation to an amount the current pressure level is below the current starting pressure level.

2. The system of claim 1, wherein the threshold amount of usage is thirty hours of therapeutic usage of the system, and wherein the gathered usage information pertains to a predetermined percentile of the pressure level of the pressurized flow.

3. The system of claim 1, wherein the one or more processors are further configured to adjust the starting level of the one or more gas parameters of the pressurized flow such that consecutive adjustments of starting levels occur at least the threshold amount of usage apart.

4. The system of claim 1, wherein, responsive to the current pressure level being below the current starting pressure level, the one or more processors are configured to operate more aggressively compared to when the current pressure level is above the current starting pressure level, by adjusting the current pressure level with an increased pressure increment, and adjusting the current pressure level responsive to fewer detected occurrences of respiratory events relative to a quantity of detected occurrences of respiratory events when the current pressure level is above the current starting pressure level.

5. The system of claim 1, wherein the levels of one or more gas parameters of the pressurized flow further include a predetermined minimum pressure level of the pressurized flow and wherein the one or more processors are further configured to replace the predetermined minimum pressure level of the pressurized flow with the determined starting level.

6. A method for determining starting levels of one or more gas parameters of a pressurized flow of breathable gas delivered during respiratory therapy of a subject having an airway, the method comprising;

generating a pressurized flow for delivery to the airway of the subject during a therapy session, wherein the pressurized flow includes breathable gas;

generating one or more output signals conveying information related to one or more gas parameters of the pressurized flow;

adjusting levels of one or more gas parameters of the pressurized flow, wherein the levels of one or more gas parameters of the pressurized flow include a current pressure level of the pressurized flow, wherein controlling the pressure generator comprises increasing and/or decreasing the current pressure level of the pressurized flow;

gathering usage information based on the provided pressurized flow;

determining a starting level of one or more gas parameters of the pressurized flow, the starting level configured to be changeable from therapy session to therapy session, wherein the determination is based on the gathered usage information, wherein the gathered usage information corresponds to respiratory therapy spanning at least a threshold amount of usage, wherein the threshold amount of usage is more than one therapy session, wherein the gathered usage information includes a pressure level of the pressurized flow, and wherein the starting level of one or more gas parameters of the pressurized flow includes a current starting pressure level, the current starting pressure level configured to be changeable from therapy session to therapy session based on the gathered usage information;

applying the starting level at a beginning of the therapy session such that the current pressure level of the pressurized flow is increased and/or decreased from the current starting pressure level;

detecting occurrences of respiratory events based on the one or more output signals; and titrating the current pressure level of the pressurized flow to a higher pressure level based on a predetermined number of respiratory events, wherein the predetermined number of respiratory events when the current pressure level is less than the current starting pressure level is lower than the predetermined number of respiratory events when the current pressure level is greater than the current starting pressure level, wherein:

responsive to the current pressure level being below the current starting pressure level, adjustments are caused using an increased pressure increment compared to a pressure increment used responsive to the current pressure level being above the current starting pressure level, and the increased pressure increment increases in relation to an amount the current pressure level is below the current starting pressure level.

7. The method of claim 6, wherein the threshold amount of usage is thirty hours of respiratory therapy, and wherein the gathered usage information pertains to a predetermined percentile of the pressure level of the pressurized flow.

8. The method of claim 6, further comprising:

adjusting the starting level of the one or more gas parameters of the pressurized flow repeatedly such that consecutive adjustments of starting levels occur at least the threshold amount of usage apart.

9. The method of claim 6, wherein, responsive to the current pressure level being below the current starting pressure level, the method operates more aggressively compared to when the current pressure level is above the current starting pressure level, by adjusting the current pressure level with an increased pressure increment, and adjusting the current pressure level responsive to fewer detected occurrences of respiratory events relative to a quantity of detected occurrences of respiratory events when the current pressure level is above the current starting pressure level.

10. The method of claim 6, wherein the levels of one or more gas parameters of the pressurized flow further include a predetermined minimum pressure level of the pressurized flow and wherein the method further comprises replacing the predetermined minimum pressure level of the pressurized flow with the determined starting level.

11. A system configured to provide respiratory therapy of a subject having an airway, the system comprising:
   means for generating a pressurized flow for delivery to the airway of the subject during respiratory therapy, wherein the pressurized flow includes breathable gas;
   means for generating one or more output signals conveying information related to one or more gas parameters of the pressurized flow;
   means for providing the pressurized flow to the subject during a therapy session;
   means for adjusting levels of one or more gas parameters of the pressurized flow, wherein the levels of one or more gas parameters of the pressurized flow include a current pressure level of the pressurized flow, wherein the means for providing the pressurized flow comprises means for increasing and/or decreasing the current pressure level of the pressurized flow;
   means for gathering usage information based on the provided pressurized flow;
   means for determining a starting level of one or more gas parameters of the pressurized flow, the starting level configured to be changeable from therapy session to therapy session, wherein the determination is based on the gathered usage information, wherein the gathered usage information corresponds to respiratory therapy spanning at least a threshold amount of usage, wherein the threshold amount of usage is more than one therapy session, wherein the gathered usage information includes a pressure level of the pressurized flow, and wherein the starting level of one or more gas parameters of the pressurized flow includes a current starting pressure level, the current starting pressure level configured to be changeable from therapy session to therapy session based on the gathered usage information;
   means for applying the starting level at a beginning of the therapy session such that the current pressure level of the pressurized flow is increased and/or decreased from the current starting pressure level;
   means for detecting occurrences of respiratory events based on the one or more output signals; and
   means for titrating the current pressure level of the pressurized flow to a higher pressure level based on a predetermined number of respiratory events, wherein the predetermined number of respiratory events when the current pressure level is less than the current starting pressure level is lower than the predetermined number of respiratory events when the current pressure level is greater than the current starting pressure level, wherein:
      responsive to the current pressure level being below the current starting pressure level, adjustments are caused using an increased pressure increment compared to a pressure increment used responsive to the current pressure level being above the current starting pressure level, and
      the increased pressure increment increases in relation to an amount the current pressure level is below the current starting pressure level.

12. The system of claim 11, wherein the threshold amount of usage is thirty hours of respiratory therapy, and wherein the gathered usage information pertains to a predetermined percentile of the pressure level of the pressurized flow.

13. The system of claim 11, further comprising:
   means for adjusting the starting level of the one or more gas parameters of the pressurized flow repeatedly such that consecutive adjustments of starting levels occur at least the threshold amount of usage apart.

14. The system of claim 11, wherein, responsive to the current pressure level being below the current starting pressure level, the system operates more aggressively compared to when the current pressure level is above the current starting pressure level, by adjusting the current pressure level with an increased pressure increment, and adjusting the current pressure level responsive to fewer detected occurrences of respiratory events relative to a quantity of detected occurrences of respiratory events when the current pressure level is above the current starting pressure level.

15. The system of claim 11, wherein the levels of one or more gas parameters of the pressurized flow further include a predetermined minimum pressure level of the pressurized flow and wherein the system further comprises means for replacing the predetermined minimum pressure level of the pressurized flow with the determined starting level.

* * * * *